(12) United States Patent
Patil et al.

(10) Patent No.: US 11,912,649 B2
(45) Date of Patent: *Feb. 27, 2024

(54) AMMONIA REMOVAL FROM UREA FINISHING

(71) Applicant: STAMICARBON B.V., Sittard (NL)

(72) Inventors: Rahul Patil, Maastricht (NL); Branislav Manic, Maastricht (NL); Petrus Anna Maria Robertus Simons, Schimmert (NL)

(73) Assignee: Stamicarbon B.V., Sittard (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/424,948

(22) PCT Filed: Dec. 30, 2020

(86) PCT No.: PCT/NL2020/050825
§ 371 (c)(1),
(2) Date: Jul. 22, 2021

(87) PCT Pub. No.: WO2021/137700
PCT Pub. Date: Jul. 8, 2021

(65) Prior Publication Data
US 2022/0089527 A1     Mar. 24, 2022

(30) Foreign Application Priority Data

Dec. 30, 2019   (EP) ..................... 19220059

(51) Int. Cl.
*C07C 273/14*     (2006.01)
*C07C 273/04*     (2006.01)
(Continued)

(52) U.S. Cl.
CPC .......... *C07C 273/14* (2013.01); *B01D 53/002* (2013.01); *B01D 53/58* (2013.01);
(Continued)

(58) Field of Classification Search
CPC .............. B01D 53/58; B01D 2251/504; B01D 2251/506; B01D 2257/406;
(Continued)

(56) References Cited

U.S. PATENT DOCUMENTS 3,944,605 A    3/1976  Inoue et al.
4,256,662 A    3/1981  Gorlovsky et al.
(Continued)

FOREIGN PATENT DOCUMENTS

CN      1031078 A    2/1989
CN      1284061 A    2/2001
(Continued)

OTHER PUBLICATIONS

Non-Final Office Action for related U.S. Appl. No. 17/424,940, dated Feb. 2, 2022. 10 pages.
(Continued)

*Primary Examiner* — Amy C Bonaparte
(74) *Attorney, Agent, or Firm* — Leason Ellis LLP (57) ABSTRACT

Disclosed is a method for the removal of ammonia from the off-gas of a finishing section of a urea production plant. Also disclosed is a corresponding urea plant, and a method of accordingly modifying a pre-existing urea plant. In a scrubbing section, the off-gas is brought into contact with an acidic scrubbing liquid so as to provide a scrubbed off-gas and a utilized scrubbing liquid comprising ammonium salt. The method specifies an evaporation section, which is part of the urea plant that produces urea melt, that is divided into first and second stages. The first stage is part of the urea melt production plant. The second stage decoupled, as regards recirculation of liquids other than the urea product stream, from the urea melt production plant. This is accomplished by sending utilized scrubbing liquid that contains ammonium salts to the second stage evaporation section, and by sending
(Continued)

condensed vapours from said second stage evaporation section to said scrubbing section.

8 Claims, 1 Drawing Sheet

(51) Int. Cl.
  *B01D 53/00* (2006.01)
  *B01D 53/58* (2006.01)
(52) U.S. Cl.
  CPC ............ *B01D 2251/504* (2013.01); *B01D 2251/506* (2013.01); *B01D 2257/406* (2013.01); *B01D 2257/80* (2013.01); *C07C 273/04* (2013.01)
(58) Field of Classification Search
  CPC ............ B01D 2257/80; B01D 53/002; C07C 273/14; C07C 273/04
  See application file for complete search history.

(56) References Cited

U.S. PATENT DOCUMENTS

| | | | |
|---|---|---|---|
| 4,539,077 | A | 9/1985 | Jonckers et al. |
| 4,821,524 | A | 4/1989 | Kostyal et al. |
| 5,744,009 | A | 4/1998 | Singh et al. |
| 7,687,041 | B2 | 3/2010 | Singh |
| 9,458,098 | B2 | 10/2016 | Mennen et al. |
| 10,370,326 | B2 | 8/2019 | Puci |
| 10,486,125 | B2 | 11/2019 | Scotto |
| 10,882,820 | B2 | 1/2021 | Mostert |
| 11,332,437 | B2 * | 5/2022 | Patil ................. C02F 1/025 |
| 2004/0054229 | A1 | 3/2004 | Meessen |
| 2009/0036712 | A1 | 2/2009 | Kojima |
| 2009/0084149 | A1 | 4/2009 | Van Der Werf et al. |
| 2011/0229394 | A1 | 9/2011 | Niehues et al. |
| 2014/0206902 | A1 | 7/2014 | Mennen |
| 2015/0026943 | A1 | 1/2015 | Mennen |
| 2015/0133689 | A1 | 5/2015 | Potthoff et al. |
| 2015/0133690 | A1 | 5/2015 | Mennen et al. |
| 2016/0184758 | A1 | 6/2016 | Soons |
| 2017/0204054 | A1 | 7/2017 | Mennen |
| 2017/0312717 | A1 * | 11/2017 | Scotto ................. B01J 2/003 |
| 2018/0326345 | A1 | 11/2018 | Doherty |
| 2019/0185422 | A1 | 6/2019 | Pustjens et al. |
| 2021/0024460 | A1 | 1/2021 | Franzrahe |

FOREIGN PATENT DOCUMENTS

| | | |
|---|---|---|
| CN | 2830398 Y | 10/2006 |
| CN | 101627009 A | 1/2010 |
| CN | 102336688 A | 2/2012 |
| CN | 203183709 U | 9/2013 |
| CN | 203578057 U | 5/2014 |
| CN | 104159888 A | 11/2014 |
| CN | 104321292 A | 1/2015 |
| CN | 104829494 A | 8/2015 |
| CN | 205307829 U | 6/2016 |
| CN | 205965056 U | 2/2017 |
| CN | 109890788 A | 6/2019 |
| CN | 110382460 A | 10/2019 |
| EP | 0302213 A1 | 2/1989 |
| EP | 2192099 A1 | 6/2010 |
| EP | 3020702 A1 | 5/2016 |
| EP | 3560907 A1 | 10/2019 |
| FR | 2095106 A5 | 2/1972 |
| GB | 1528051 | 10/1978 |
| JP | S58-189153 A | 11/1983 |
| WO | 2010060535 A1 | 6/2010 |
| WO | 2012161620 A1 | 11/2012 |
| WO | 2013165245 A1 | 11/2013 |
| WO | 2013165246 A1 | 11/2013 |
| WO | 2014188371 A1 | 11/2014 |
| WO | 2016099269 A1 | 6/2016 |
| WO | 2021/137699 A1 | 7/2021 |
| WO | 2021/137701 A1 | 7/2021 |

OTHER PUBLICATIONS

Notice of Allowance for related U.S. Appl. No. 17/424,958, dated Mar. 10, 2022. 26 pages.
International Search Report and Written Opinion in corresponding International Patent Application No. PCT/NL2020/050824 dated Mar. 23, 2021. 9 pages.
International Preliminary Report on Patentability in corresponding International Patent Application No. PCT/NL2020/050824 dated Jun. 29, 2021. 11 pages.
International Search Report and Written Opinion in corresponding International Patent Application No. PCT/NL2020/050825 dated Mar. 23, 2021. 9 pages.
International Search Report and Written Opinion in corresponding International Patent Application No. PCT/NL2020/050826 dated Mar. 10, 2021. 11 pages.
International Preliminary Report on Patentability in corresponding International Patent Application No. PCT/NL2020/050826 dated Jun. 17, 2021. 12 pages.
Meessen. Ullmann's Encyclopedia of Industrial Chemistry. "Urea." Wiley-VCH Verlag Gmbh & Co. KGaA, Weinheim (2010). 10.1002/14356007.a27_333.pub2. 39 pages.
No Author. "Urea Synthesis: A Status Report—I." Nitrogen No. 185, May-Jun. 1990. pp. 22-29.
Potthoff. "Innovative Ammonia Emission Reductions." Nitrogen + Syngas 294, Jul.-Aug. 2008, pp. 39-41. XP-002525996. 4 total pages.
Van Der Zande. "Zero waste urea production." Fertilizer Focus, Mar.-Apr. 2018. 3 pages.
Notification of Registration of the Grant of Patent Right in Chinese Application No. 202080091183.6, dated Oct. 10, 2022.
Office Action and English translation for corresponding Japanese Application No. 2022-540527, dated Feb. 6, 2023.

* cited by examiner

AMMONIA REMOVAL FROM UREA FINISHING

CROSS-REFERENCE TO RELATED PATENT APPLICATIONS

This application is a U.S. National Stage Application under 35 U.S.C. § 371 of International Patent Application No. PCT/NL2020/050825 filed Dec. 30, 2020, which claims the benefit of priority of European Patent Application No. EP 19220059.0 filed Dec. 30, 2019, both of which are incorporated by reference in their entireties. The International Application was published on Jul. 8, 2021, as International Publication No. WO 2021/13770 A1.

FIELD OF THE INVENTION

The invention is in the field of the removal of ammonia from the off-gas of a finishing section of a urea production plant. Particularly, the invention pertains to processing of ammonium salt solution resulting from such ammonia removal.

BACKGROUND OF THE INVENTION

Urea is produced from ammonia and carbon dioxide. Today's urea production involves relatively clean processes, particularly low in the emission of urea dust and ammonia. However, besides the chemical synthesis of urea, the production of urea on a commercial scale requires that the urea be presented in a suitable solid, particulate form. To this end, urea production involves a finishing step in which a urea melt is brought into the desired particulate form, generally involving any one of prilling, granulation, or pelletizing. As a result of these processes ammonia is released, thus ending up in an off-gas stream of urea finishing. Conventionally, after being cleaned in a scrubbing system, this air is vented to the atmosphere.

With a view to increased demand for urea production, and increased legal and environmental requirements as to reduce the level of emission of ammonia, it is desired that the ammonia specifically emitted in urea finishing, be prevented or removed. This cannot generally be done by just scrubbing with water. Moreover, in some of these finishing processes, particularly granulation and prilling, large amounts of ambient air are used as a coolant. As a result the concentration of ammonia in such vented air streams is low, which makes ammonia removal even more challenging. E.g., for a large plant (producing more than 3500 metric tonnes per day, a typical airstream is of the order of 750 000 $Nm^3/h$. A typical concentration of ammonia therein is 100 $mg/Nm^3$. The state of the art in the present field is the removal of ammonia by acid scrubbing. Generally this involves an additional scrubbing section downstream of scrubbing with water. Thereby, an acid such as sulfuric acid or nitric acid is used for washing out ammonia, resulting in formation of an ammonium salt solution. This solution can be purged out of the battery limit but, preferably, is processed by reworking it within the urea process. In the latter case, after removal of water, the salt is reprocessed in a urea finishing section, together with virgin urea melt However, the reworking of ammonium salts in a urea process is not straightforward.

Figure 1:
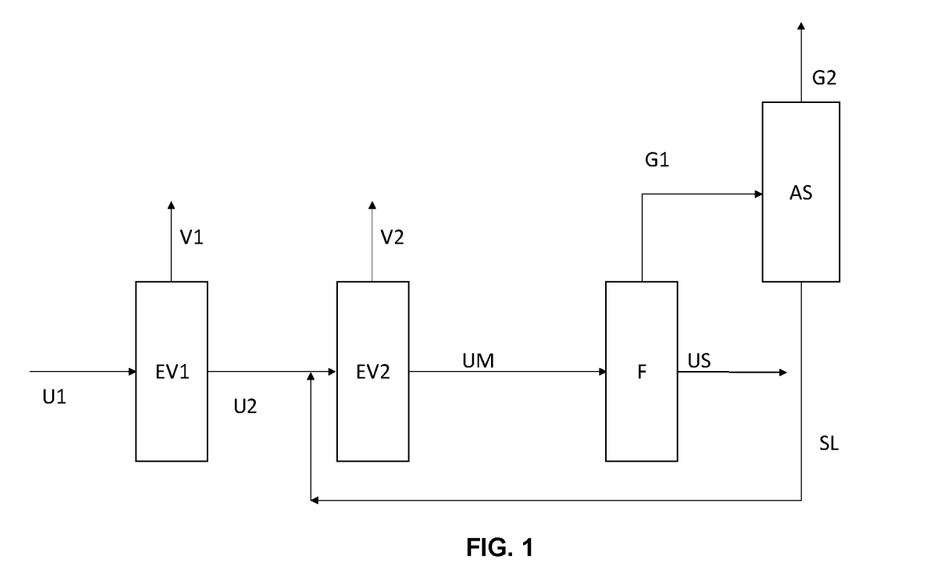
FIG. 1 shows a scheme for the processing of ammonium salt solution from urea finishing in accordance with the invention.

A background reference is M Potthoff, Nitrogen+Syngas, [online], July. August 2008, pages 39-41. In FIG. 1 of said background reference a combined dust and acidic scrubber system is shown. The ammonia is absorbed in the acidic scrubbing section and converted into ammonium sulphate. The ammonium sulphate solution is added to the recycle flow going back to the evaporation section. Therein the ammonium sulphate solution is mixed with urea melt from the urea synthesis section. The condensate obtained from the evaporation section is sent to said combined dust and acidic scrubber system.

This process has several drawbacks. These are addressed in WO 2010/060535, which inter alia cautions that in the aforementioned disclosure the water balance in the system is a critical parameter. If disturbed, the urea synthesis will be contaminated with ammonium salt. Or, alternatively, large amounts of waste water need to be treated. In fact, the process of the aforementioned FIG. 1 of said background reference results in the generation of large amounts of condensate contaminated with ammonium salt. This is typically caused by entrainment of salt within the vapour to be condensed. As acknowledged in WO 2010/060535, ammonium salts should be avoided in the urea process and cannot easily be processed at existing urea facilities. E.g., concentrating the ammonium salt solution in the existing evaporation section of a urea melt plant is not considered viable. As this would result in a contamination of the process streams in the urea plant with a salt, corrosion issues would occur. Moreover, these problems are not limited to the process streams, but may also affect equipment in the steam circuit of a urea plant. In a urea plant normally a water purification section is present. Reworked ammonium salt will also end up in the purified process condensate coming from such water purification, which is frequently used as make-up water for steam generation boilers. The corrosion issues related to the presence of ammonium salts, can thus extend to these boilers.

In fact, as explained in WO 2010/060535, a conventional urea production facility has only a limited set of options to reduce gaseous ammonia emissions from the granulation plant: to discharge the diluted ammonium salt solution to a waste water stream; to concentrate the diluted ammonium salt solution up to a concentration which can be utilized by other plants, e.g. in fertilizers (NPK); to produce UAS (urea/ammonium sulphate) fertilizer with a high sulphur content; to produce UAN (urea/ammonium nitrate) solution.

All of these alternatives require significant investments and changes to operating conditions or entail changes of the product composition and characteristics. All above options result in new products that require additional facilities for transport and handling as well as energy utilities in expensive quantities.

The aforementioned Potthoff 2008 disclosure does not present a solution how to deal with the necessarily large amounts of water containing ammonium sulphate that are generated in the finishing section. In order to solve this problem, WO 2010/060535 proposes a relatively complicated scrubbing system in a finishing section for a urea plant, including a separate evaporation section. Essentially, the scrubbing system in itself is a complete closed system, and therefore totally decoupled from urea synthesis.

A disadvantage hereof is that a urea finishing section, or a separate urea finishing plant, needs to be provided with additional equipment dedicated to the evaporating, generally with urea solution, of the ammonium salt solution.

The present invention concerns a method for the removal of ammonia from urea finishing, comprising neutralizing the ammonia with acid as is the current standard. Thereby the invention seeks to provide a method that allows avoiding the installation of an additional evaporation section, yet also seeks to avoid contamination of process streams in a urea production facility.

SUMMARY OF THE INVENTION

In order to better address one or more of the aforementioned problems, the invention provides, in one aspect, a method for the removal of ammonia from the off-gas of a finishing section of a urea production plant, wherein the finishing section operates to convert a urea melt into solid urea products, thereby generating ammonia-containing off-gas; said urea melt being obtained by evaporating water from an aqueous urea solution in a first stage evaporation section, so as to form a concentrated urea solution, and further evaporating water from said concentrated urea solution in a second stage evaporation section so as to form the urea melt; the method comprising subjecting the off-gas to contact with an acidic scrubbing liquid so as to provide a scrubbed off-gas and a utilized scrubbing liquid comprising ammonium salt; wherein the method comprises sending utilized scrubbing liquid to said second stage evaporation section, thereby subjecting it to evaporation of water together with the concentrated urea solution.

In another aspect, the invention presents a method for the production of solid urea, comprising producing an aqueous urea solution, evaporating water from said aqueous solution in a first stage evaporation section so as to form a concentrated urea solution, further evaporating water from the concentrated urea solution in a second stage evaporation section into a urea melt, and subjecting the urea melt to finishing so as to convert it into solid urea products, thereby generating ammonia-containing off-gas; subjecting said off-gas to contact with an acidic scrubbing liquid so as to provide a scrubbed off-gas and a utilized scrubbing liquid comprising ammonium salt; the method comprising sending utilized scrubbing liquid to said second stage evaporation section, thereby subjecting it to evaporation of water together with the concentrated urea solution.

In yet another aspect, the invention is a method of modifying an existing urea plant, the existing plant comprising a production section for urea melt having a liquid urea connection to a finishing section for converting the urea melt into solid urea products, whereby the production section comprises an evaporation section for converting produced aqueous urea solution into urea melt, and a water purification section downstream of the evaporation section, said evaporation section comprising a liquid outlet for sending condensed vapours to the water purification section, wherein the method comprises adapting the evaporation section so as to provide a first stage evaporation section having a liquid outlet for concentrated urea solution and a gas outlet to a first stage condenser, and a second stage evaporation section downstream from the first stage evaporation section, said second stage evaporation section comprising a second stage evaporator having a gas outlet to a corresponding second stage condenser, the first stage condenser having a liquid outlet for sending condensed vapours to the water purification section, wherein the method further comprises providing the second stage evaporation section with an connection to an outlet for utilized scrubbing liquid from a scrubbing system of the finishing section, particularly for utilized scrubbing liquid that comprises ammonium salt, and providing the corresponding second stage condenser with a connection for sending condensed vapours to a scrubbing system in the finishing section.

In a still further aspect, the invention provides a plant for the production of solid urea products, the plant comprising a production section for urea melt having a liquid urea connection to a finishing section for converting the urea melt into solid urea products, whereby the production section comprises an evaporation section for converting produced aqueous urea solution into urea melt, and a water purification section downstream of the evaporation section, said evaporation section comprising a first stage evaporation section comprising a first stage evaporator having a liquid outlet for concentrated urea solution and a gas outlet to a first stage condenser, and a second stage evaporation section downstream from the first stage evaporation section comprising a second stage evaporator and a second stage condenser, wherein the first stage condenser has a liquid outlet for sending condensed vapours to the water purification section, whereby the second stage evaporator has a connection to an outlet for utilized scrubbing liquid from a scrubbing system of the finishing section, and wherein said second stage evaporator has a gas outlet to a second stage condenser, wherein said second stage condenser has a liquid connection for sending condensed vapours to a scrubbing system in the finishing section.

DETAILED DESCRIPTION OF THE INVENTION

The invention, in a broad sense, allows recycling ammonium salt solution from the off-gas treatment of urea finishing back to the existing evaporation section of a urea melt production plant, while reducing, and preferably avoiding, the risk of contaminating process streams in the melt plant with salt.

Hereinafter this disclosure will initially make reference to the method of the invention. This generally relates to the aforedescribed method for the removal of ammonia, as well as the method for the production of solid urea. Unless specified otherwise, the embodiments thereby described are applicable to all methods disclosed herein, as well as to the plant of the invention and the method of modifying a plant. To the extent that these embodiments are worded in terms of process steps, it will be understood that this relates to corresponding features of a plant suitable for conducting such process steps.

Where, in this description, it is spoken of "fluid communication", this refers to any connection between a first part or section of a plant and a second part or section of a plant via which fluids, including liquids and gases, can flow from the first part of the plant to the second part of the plant. In the event of liquids, such fluid communication is typically provided by piping systems, hoses, or other devices well-known to the skilled person for the transportation of fluids. In the event of gases, such fluid communication is typically provided by gas flow lines. Such gas flow lines typically comprise piping systems, ducts, or other devices well-known to the skilled person for the transportation of gases, if needed under pressures that are above atmospheric pressures or below (vacuum). A "liquid inlet" is an inlet suitable for allowing liquid to enter. A "liquid outlet" is an outlet suitable for allowing liquid to exit. Analogously, a "gas inlet" and "gas outlet" allow the entry, respectively the exit, of gas. The terms "gas" and "vapour" are used interchangeably, whereby "vapour" is generally used to indicate the presence of water in the gaseous state.

Generally, a solid urea product will be allowed to contain up to 5 wt. % of contaminations and/or solid components other than urea, and this hampers the incorporation of ammonium salts, unless a combined product such as UAS were intentionally produced.

It will be understood that the method of the invention does result in ammonium salt being incorporated into the urea product stream of a urea production plant. Judiciously, however, this is done at a stage in which the urea product stream is in the form of a concentrated aqueous urea solution, i.e., an aqueous solution having a higher concentration of urea than the aqueous urea solution produced in urea synthesis, prior to being subjected to evaporation. As a result, the amount of salt incorporated into the urea product stream forms a relatively lower amount relative to the urea in such stream. The solid urea product of the present invention comprises e.g. at least 46 wt. % N and comprises e.g. 0.10 to 5 wt. % ammonium salt. The solid urea product may comprises e.g. up to 5.0 wt. % solid components other than urea, such as including micronutrients. In some embodiments, the solid urea product can be described as UAS fertilizer (urea ammonium sulphate fertilizer).

This is based on the judicious insight not to recycle the ammonium salts to upstream of the full evaporation section, but to a downstream evaporator therein. Accordingly, as mentioned above, the method of the invention comprises sending utilized scrubbing liquid to a second stage evaporation section. It will be understood that sending utilized scrubbing liquid to a second stage evaporation section, means that this liquid is sent to said second stage evaporation section without passing via a first stage evaporation section. In fact, the second stage evaporation section is, by definition, formed by the evaporator to which the ammonium salt solution is sent, and any evaporators downstream thereof. The utilized scrub liquid comprises urea and ammonium sulphate.

The method comprises sending at least a part and preferably all of the utilized scrubbing liquid to a second stage evaporation section by adding said utilized scrub liquid to the concentrated urea solution, with e.g. 90-98 wt. % urea, formed in the first stage stage evaporation section, wherein the first stage evaporation section preferably operates at a pressure of less than 1.0 bara (bar absolute). The method comprises preferably sending concentrated urea solution from the first stage evaporation section through a flow line to said second stage evaporation section and adding said utilized scrub liquid to the concentrated urea solution for example inside said flow line between the first stage evaporation section and the second stage evaporation section. The method preferably comprises concentrating the urea solution e.g. from the high pressure stripper by water removal by evaporation to reduce the water content with at least 10% percentage point to give concentrated urea solution, and adding at least a part and preferably all of the utilized scrubbing liquid containing ammonium salts to said concentrated urea solution upstream of a further evaporation step to even further concentrate the urea solution, wherein the further evaporation step is carried out at a low pressure such as below 20 kPa or below 10 kPa.

In order to benefit from the invention, it is not required that all of the utilized scrubbing liquid containing ammonium salts is recirculated as described. It is conceivable that part of said utilized scrubbing liquid is collected elsewhere, e.g., sent to battery limit. Generally, at least 25% of the utilized scrubbing liquid from acidic scrubbing is sent to the second stage evaporation section, such as at least 50%, preferably at least 75%, such as 95% to 100% by weight. More preferably, substantially all of said utilized scrubbing liquid is sent to the second stage evaporation section.

Preferably the method comprises adding the utilized scrubbing liquid to the concentrated urea solution obtained from the first stage evaporator. In another preference, the utilized scrubbing liquid is added to a flow line for concentrated urea solution from the first stage evaporator to the second stage evaporator. It is customary for such evaporation sections to comprise at least two evaporators placed in series, and this necessarily holds for a plant in which the present method is operated. In conducting the method of the invention in a urea production plant having two such evaporators, the first, upstream evaporator will function as the first stage evaporation section. In that event the second, downstream evaporator will function as the second stage evaporation section. It is noted that the first stage and second stage evaporation sections according to the invention will preferably comprise vacuum evaporators. In a urea plant a recovery section, more typically a low pressure recovery section, may comprise an evaporator, typically a pre-evaporator. A pre-evaporator operates e.g. at 80° C. to 100° C. and/or gives a concentrated urea solution with e.g. 70 to 85 wt. % urea, e.g. 75-85 wt. % urea (including biuret). It will be understood that such an evaporator does not function as part of the evaporation section. The evaporation section, including the first and second stage evaporation sections of the invention, are generally placed downstream of urea synthesis (producing urea aqueous solution), serve to produce urea melt, and are positioned upstream of urea finishing (solidifying urea melt).

The evaporation sections according to the invention in either or both stages optionally comprise more than two evaporators placed in series. The method of the invention then can be applied by sending the ammonium salt solution to any one of the evaporators downstream of the first evaporator. This results in one or more evaporators being upstream of the evaporator to which the ammonium salt solution is sent. These one or more upstream evaporators accordingly form the first stage evaporation section. The second stage evaporation section is, by definition, formed by the evaporator to which the ammonium salt solution is sent, and any evaporators downstream thereof.

Customarily, the water evaporated in the evaporation section of a urea melt plant, is subjected to condensation. The condensed vapours are recirculated, generally to a water purification section. As mentioned, the presence of ammonium salts in the urea production process incurs a risk to affect the steam circuit of a urea plant. As a result of sending the ammonium salt solution to the second stage evaporation section, the water removed in the first stage evaporation section can be recirculated in the conventional manner without presenting such risk.

It is hereby noted that the presence of (inorganic) ammonium salts in the liquid (such as ammonium sulphate or ammonium nitrate) can lead to ammonium salts in the condensed vapour due to entrainment. In this way ammonium salts can end up in the waste water treatment system, if not dealt with. The invention is based on the judicious insight that the amount of water removed in the second stage evaporation section is significantly lower than in the first stage evaporation section. By adding the scrubbing liquid from the finishing section to the second evaporation stage, the inventors found that the water balance works and yet contamination of the urea process with ammonium salt can be avoided.

In essence, the second stage evaporation section becomes an integral part of the finishing section, while still also being part of the urea synthesis plant (i.e., a urea melt plant). The second stage evaporation section and the finishing section form a closed loop with respect to ammonium salt-containing streams.

The present invention thereby has an additional advantage for urea production, particularly in the field of fertilizers. Frequently additional nutrients are added to urea fertilizers. As a result of the present insights, these nutrients can now be added to the urea melt before sending this tot the finishing section. In conventional urea plants this cannot be done. The present invention makes it possible to add any nutrients here that are readily soluble in water. In fact, advantageously any finishing process enhancers can be added without affecting the urea synthesis process.

Yet a further advantage relates to the use, as is customary in the field, of formaldehyde as a granulation additive. In the traditional melt/granulation plant set-up, a urea solution is recycled from granulation to the urea synthesis plant (urea melt plant). This solution inevitably contains a small amount of Urea-formaldehyde (UF), as a result of using formaldehyde in granulation. After processing of this urea solution over the evaporators, a small amount of UF will then also end up in the water purification section of the urea melt plant. Therein a part of UF is dissociated over the hydrolyzer resulting in formic acid. The formic acid reacts with the ammonia resulting in ammonium formate. The presence of ammonium formate in the water purification section, causes a limitation on the lowest ammonium concentration, which could be achieved in the purified process condensate. The present invention also solves this issue, where the urea solution from granulation, containing ammonium salt but also a small amount of UF, is recycled back to the second stage evaporation section.

In view of the above, it is preferred to avoid recirculation to the water purification section of condensed vapours obtained from the second stage evaporation section. I.e., from the evaporation section to which the ammonium salt solution is sent. To this end, the method of the invention preferably comprises sending vapour condensate obtained from the second stage evaporation section, to a scrubbing system of the finishing section, preferably to the scrubber where the off-gas is contacted with acidic scrubbing liquid.

As mentioned, the second stage evaporation section optionally comprises more than one evaporator in series. In this embodiment, preferably at least the vapour condensate of the last, downstream evaporator of the second stage evaporation section will be sent to the scrubbing system of the finishing section. Preferably, the vapour condensate from a plurality, and preferably all, of the evaporators of the second stage evaporation section is sent to a scrubbing system of the finishing section. This has the advantage of securing that no ammonium salt residue at all is prone to end up in the water and steam circuit of the urea production plant.

It will be understood that the method of the invention requires a corresponding arrangement of the equipment in which the method is conducted. Thus, the second stage evaporation section, or at least one second stage evaporator, has an inlet for utilized scrubbing liquid from a scrubbing system of the finishing section, or otherwise a connection to an outlet for said utilized scrubbing liquid, particularly utilized scrubbing liquid from acidic scrubbing. Taking into account the embodiment in which vapour condensate of the second stage evaporation section is sent to the scrubbing system in the finishing section, the second stage evaporation section has a liquid connection for sending condensed vapours to a scrubbing system in the finishing section. More specifically, in such embodiment, at least one second stage evaporator has a gas outlet to a second stage condenser, and said second stage condenser has a liquid connection for sending condensed vapours to a scrubbing system in the finishing section.

The invention also pertains to a method for the production of solid urea as described hereinbefore. The embodiments described for the method for the removal of ammonia from the off-gas of a finishing section of a urea production plant, are all also applicable to the method of producing solid urea, such as prilling, granulating, or pelletizing. The solid urea preferably is in the form of prills or granules. In the method for the removal of ammonia, the finishing section is, e.g., a pelletizer, and is preferably a prilling tower or a granulator, such as a spouted bed granulator or, preferably, a fluid bed granulator.

In urea prilling, urea melt is supplied at the top of a prilling tower, and distributed as droplets. The urea melt droplets solidify as they fall down while cooling against a large quantity of upward-moving air. Urea prills are withdrawn from the bottom. The fresh cooling air enters the bottom of the prilling tower. The off-gas comprising urea and ammonia leaves the prilling tower near the top.

Emissions can for example be 0.5 to 2.5 kg urea dust per ton urea prills (35 to 125 mg/Nm$^3$) and about 0.5 to 2.7 kg NH3 per ton (35-245 mg/Nm$^3$). An example indicative air flow for a urea prilling tower is 500 000 Nm$^3$/hr. A larger urea prilling tower may for instance have 900 000 Nm$^3$/hr off gas, with a urea capacity of 75-100 mt/hr (metric ton per hour).

In an interesting embodiment, the finishing section comprises a prilling tower and the downstream second stage condenser is a chilled condenser or a chilled condensation section.

The chilled condenser or condensation section preferably uses a cooling medium (cooling fluid) other than water, or uses for instance chilled water as cooling medium. Typically, the chilled condenser comprises a heat exchanger having a first side and a second side separated by at least a heat-exchanging wall and optionally by a further compartment for a heat transfer fluid. In an embodiment, the vapor to be condensed is provided on the first side and chilled cooling medium is received on the second side. The first side and second side can, in addition to being separated by said wall, be separated by a further compartment for a heat transfer fluid such as water. The chilled cooling medium is typically supplied to an inlet of the condenser, at said second side, from a chiller. In the chiller, the cooling medium is chilled, for instance by at least 5° C. or at least 10° C. and/or to a temperature of less than 25° C. The chilled cooling medium at the inlet of the chilled condenser typically has a lower temperature than the cooling water that is used elsewhere in the urea plant and urea production process, e.g. at least 5° C. lower or at least 10° C. lower. Cooling water is for instance used in a first condenser connected to a second evaporator arranged upstream of the first evaporator. The chilled cooling medium at the inlet of the chilled condenser typically has a temperature lower than the ambient temperature, e.g. at least 5° C. lower or at least 10° C. lower.

The term 'cooling medium' as used herein generally refers to a cooling fluid.

In some embodiments, the temperature of the cooling medium is for instance higher than 0° C. to avoid freezing of water in the process side of the condenser, and preferably temperature of cooling medium is at least 5° C., e.g. 5 to 10° C., e.g. at about 5° C.

The chiller is for instance a vapor-compression refrigeration system, comprising a compressor, condenser, expansion valve, and evaporator, connected by a loop for cooling medium. In a preferred embodiment, chilling of the cooling medium in the chiller involves subjecting the cooling medium received in the vapor phase from the cooling fluid side of the chilled condenser to compression to a higher pressure, condensation with heat withdrawal at said higher pressure, and expansion to a lower pressure to give chilled liquid cooling medium.

Advantageously, a chilled condenser can be used for efficiently transporting the vapor from the downstream second stage evaporator to the second stage condenser without using a booster ejector and without adding steam into the second vapor. In this way, the amount of liquid obtained from the downstream second condenser advantageously remains small even if the second stage evaporator operates at a low pressure such as below 10 kPa.

The cooling medium other than water that is preferably used in the chilled condensation section is e.g. $NH_3$ or a halogenated hydrocarbon.

Generally, by way of preference, in the event of urea finishing by means of a prilling tower, the evaporation section comprises evaporation in two stages, whereby a second evaporator operates at deep vacuum (less than 20 kPa). This facilitates producing a urea melt desirably containing less than 2.5 wt. % water. In accordance with the present disclosure, the second evaporator could form, or be comprised in, the second stage evaporation section. As a result of the recirculation of utilized scrubbing liquid to said second stage evaporation section, the aforementioned second evaporator will receives more water. As result, a relatively larger amount of very low pressure vapour is produced. In order to condense this, preferably, a chilled condenser is used. An alternative would be the use of a booster ejector, but this will result in a further increase of the amount of water coming off the second condenser. Limiting this amount of water (condensed vapours from second stage evaporation) is desired, particularly in view of exercising the possibility that such water is used as scrub liquid water in the off-gas scrubber.

In a fluid bed granulator, a fluidized bed of particles is maintained in one or more granulation compartments by supplying fluidization gas, often air, through a fluidization plate. This plate is arranged at the bottom of said compartments and has numerous openings for fluidization gas. In operation of the device, granulation liquid (e.g. urea melt, such as with more than 90 wt. % or more than 95 wt. % urea) is supplied into the fluidized bed using nozzles in the fluidization plate. The nozzles also use secondary gas, often air, which gas is for example used in the nozzles for atomization of the granulation liquid into a spray or for transport of the particles through a film of the granulation liquid, which film is formed by a film-forming nozzle. In each granulator compartment, the nozzles are typically provided in an array in the fluidization plate. In operation, the fluidization gas goes up through the openings in the fluidization plate, to ensure the fluidization of the particles in the granulation compartments and to take away crystallization heat.

The aforementioned aspects of the invention are conducted on the basis of providing an aqueous urea solution. Preferably, the method of the invention thereby comprises producing the aqueous urea solution in a urea synthesis plant. Such urea synthesis plant can be part of a plant for the production of urea as such, or of urea-based products such as urea ammonium nitrate or urea ammonium sulphate.

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis section. Typical urea production plants further comprise a recovery section and a finishing section. In the recovery section non-converted ammonia and carbon dioxide are recovered and recirculated to the synthesis section. Downstream of the recovery section, an evaporation section generally follows. Therein the urea concentration is further increased by the evaporation of water, resulting in a highly concentrated solution that is generally referred to as a urea melt. Generally, a urea melt will have a concentration of more than 90 wt. % of urea, more typically more than 95 wt. % of urea. The concentration in the aqueous solution produced by a urea plant before evaporation, is generally 60 to 90 wt. % urea, such as 65 to 85 wt. % urea.

In the finishing section, typically, the urea melt is brought into a desired solid, particulate form, generally involving techniques such as prilling, granulation, or pelletizing. The melt to be processed in a finishing section will generally have a water content of below 5 wt. %. E.g., a granulator typically requires the urea melt to have a urea content of at least 97.5 wt. %. In the event that the finishing involves prilling, this will usually require the urea melt to have a water content of less than 1.0 wt. % or less than 0.50 wt. %.

In the evaporation section still considerable amounts of CO2 and particularly NH3 are removed. By treatment of non-condensed vapours from the evaporation section in a scrubber, the ammonia is removed. Condensed vapours go to a waste water treatment unit (herein also referred to as a water purification section) which is a very costly and energy intensive operation. In this section urea (entrained in the condensed vapours) is eventually hydrolysed to ammonia and CO2 (typically at a temperature of 180-230° C.), followed by desorption ammonia and carbon dioxide.

Thus, in essence, a urea plant conventionally comprises a urea synthesis section in which CO2 and NH3 are converted into urea, a carbamate recovery section in which residual CO2 and NH3 are recovered and recirculated to the synthesis section, and a water purification section downstream of the evaporation section. Generally the invention will be implemented in a plant of this type.

The urea production process (e.g., the synthesis section and recovery section design) is not particularly restricted, for instance a process with a high pressure stripper can be used, wherein the high pressure stripper uses for instance CO2 or NH3 as strip gas, or self-stripping. A total recycle design or a partial recycle design without a high pressure stripper can also be used, or even a once-through design. Such designs are well known in the art and are described for instance in Ullmann's Encyclopedia of Industrial Chemistry, chapter Urea (2010).

Preferably, the urea production plant is a so-called CO2 stripping plant. Therein the synthesis section comprises a urea synthesis loop comprising a reactor, a CO2 stripper downstream of the reactor, and carbamate condenser for condensing gas from the stripper, wherein the reactor is downstream of the condenser.

In the invention, the process condensate of a second stage evaporation section, which is prone to contain entrained urea and entrained ammonium salt, is preferably sent to the scrubbing system of the finishing section, rather than to the water purification section of the urea production plant. This provides an opportunity to incorporate the resulting amounts of urea (containing ammonium salt) directly into a final product stream, instead of customarily dissociating said urea using a hydrolyser in the water purification section first, and recirculating the resulting ammonia and carbon dioxide to the synthesis section of the melt plant (i.e., the urea production plant from which a urea melt is obtained).

Sending vapour condensate from the second stage evaporation section to the finishing section rather than recirculating it to the urea production plant, comes with an additional and unexpected benefit. Effectively, in comparison with a conventional urea production plant and process, a relatively lower amount of water from evaporation will end up in the water purification section of the urea production plant. As a result, the latter section is unloaded substantially. Thus, if the method of the invention is implemented in building a new plant (i.e., a so-called grassroots situation), the water purification section can be designed smaller than conventional. This has clear advantages from the point of view of both space and costs. In the event of modifying an existing urea production plant (i.e., a so-called revamping situation) this has the advantage that a larger capacity and/or higher efficiency obtained elsewhere in the plant, does not need to be accompanied with a corresponding enlargement of the capacity of the water purification section. Since water purification sections are costly and form a large part of a plant, with generally limited space available for expansion, this is a considerable advantage of the method the invention. As a further advantage, the amount of utilized make-up water in the scrubbing system is reduced substantially. Make-up water is used for overcoming water losses due to evaporation of the recirculating scrubbing solution when brought in contact with hot unsaturated exhaust air/off gas from the finishing section. Typically, purified process condensate is used as a make-up water. Purified process condensate can for instance also be used as boiler feed water.

The aforementioned splitting of the vapour condensation output from the evaporation section, comes with a further advantage. As indicated above, a relatively lower amount of urea will need to be dissociated (hydrolyzed) in the water purification section (i.e., the waste water treatment section). This essentially refers to an amount of urea that initially is produced in the synthesis section, then is dissociated in the water purification section, and thereafter, from recirculated ammonia and carbon dioxide effectively is created again in the synthesis section. In this embodiment, a plant according to the present disclosure thus makes use of the urea starting materials more effectively than plants from before the present disclosure.

In a preferred embodiment, the plant is operated in conducting the above-described method of removing ammonia from a urea finishing section. To this end, the scrubbing system of the finishing section typically comprises at least two scrubbers in series, wherein an upstream scrubber is a dust scrubber and a downstream scrubber is an acid scrubber. Herein upstream and downstream refer to the direction of the off-gas stream. It will be understood that the scrubbing system, preferably the acid scrubber, will then have a liquid connection to the inlet for utilized scrubbing liquid provided in the second stage evaporation section. The utilized scrub liquid contains e.g. urea that is captured from the off-gas in the dust scrubber and ammonium salt from the acid scrubber. The ammonium salt is formed by the reaction of an acid with $NH_3$ in the acid scrubber. The $NH_3$ is scrubbed from the off-gas in the acid scrubber. The utilized scrubbing liquid comprises e.g. at least 10 wt. % or at least 30 wt. % urea, e.g. up to 60 wt. % urea. The utilized scrub liquid is e.g. purged from the scrubbing system, wherein e.g. the scrub liquid is recirculated in the scrubbing system.

Well known providers of dust scrubbing systems are Envirocare®, Hamon, Waterleau, and others. The workings of these scrubber systems are well-known to anybody skilled in the art. Quite commonly in these scrubbing systems the off-gas (air) is washed with circulating urea solution of relatively low concentration. Thereby typically 45 wt. % urea solution is controlled prior to purging it into the urea plant. Inside the scrubbing system it is possible that more than one circulation of urea solution is present. The resulting urea solution is partially purged, and thereby typically merged with fresh urea solution from the melt plant. Generally, this is done upstream of the evaporation section, and generally the condensed vapours resulting therefrom are send (via absorbers) to the water purification section of the urea production plant.

It will be understood that, in accordance with the present invention, the urea solution resulting from the scrubbing system is sent to a second stage evaporation section as explained above. A further benefit of this arrangement, is that the installation of an additional dedicated evaporation section in the finishing section can be avoided.

It will be understood that in view of the desired ammonia-removal, a dust scrubbing system in the finishing section is provided with an additional section for washing out ammonia. To wash ammonia efficiently, preferably a mineral acid, like sulfuric acid or nitric acid is applied. Other suitable acids include, e.g. phosphoric acid, citric acid, acetic acid. The acid reacts with the ammonia to form an ammonium salt in water. The resulting ammonium salt solution can still be partially purged. Preferably, all of the ammonium salt solution is processed via a second stage evaporation section as described hereinbefore.

These dust and ammonia scrubbing stages can be conducted in two or more scrubbers in series. Preferably, both scrubbing stages are conducted in a single apparatus. The circulation of the two scrubbing liquids hereby involved, can be kept separate. If implemented in a single unit, the upper (acid) scrubbing liquid will overflow the bottom (dust) scrubbing section.

The present invention lends itself advantageously to modifying an existing urea plant. Generally, such an existing plant comprises a production section for urea melt. This production section has a liquid urea connection to a finishing section for converting the urea melt into solid urea products. Thereby the production section comprises an evaporation section for converting produced aqueous urea solution into urea melt, and a water purification section downstream of the evaporation section. The evaporation section in the existing plant will typically comprise at least two evaporators in series, each having a gas outlet to corresponding condensers. Said condensers have a liquid outlet for sending condensed vapours to liquid inlet of the water purification section.

The modification method of the invention comprises providing at least one second stage evaporator with a connection to an outlet for utilized scrubbing liquid from a scrubbing system of the finishing section, and changing the liquid outlet of the corresponding second stage condenser from a connection to the water purification section into a connection for sending condensed vapours to a scrubbing system in the finishing section. This modification makes it possible to conduct in the modified plant, the aforementioned methods of removing ammonia from the off-gas of this finishing section, and the corresponding production of solid urea.

The aforedescribed methods can also be conducted in a newly built plant. This plant will generally have the same features as the modified plant.

Accordingly, the plant comprises a production section for urea melt having a liquid urea connection to a finishing section for converting the urea melt into solid urea products. Thereby the production section comprises an evaporation section for converting produced aqueous urea solution into urea melt, and a water purification section downstream of the evaporation section. The evaporation section comprises a first stage evaporator having a liquid outlet for concentrated urea solution and a gas outlet to a first stage condenser, and at least one second stage evaporator downstream from the first evaporator, wherein the first stage condenser has a liquid outlet for sending condensed vapours to the water purification section, whereby at least one second stage evaporator has an inlet for utilized scrubbing liquid from a scrubbing system of the finishing section, or otherwise a connection to an outlet for said utilized scrubbing liquid, and wherein said second stage evaporator has a gas outlet to a second stage condenser, wherein said second stage condenser has a liquid connection for sending condensed vapours to a scrubbing system in the finishing section.

The invention will hereinafter be further illustrated with reference to the drawings.

FIG. 1 shows a scheme for the processing of ammonium salt solution from urea finishing in accordance with an example embodiment of the invention.

An aqueous urea solution (U1) of, e.g., 70 wt. % urea concentration is sent to a first stage evaporation section (EV1), such as a single evaporator. This evaporator produces a concentrated urea solution (U2) of, e.g., 90-98 wt. % urea concentration. The evaporation section has an outlet for vapours (V1) necessarily obtained as a result of evaporation (indicated in the figure as "water"). The concentrated urea solution is fed to a second stage evaporation section (EV2), such as a single evaporator. Therein, under removal of water by evaporation (for which the evaporation section has a water (vapour) outlet (V2) as shown), a urea melt (UM) of urea concentration of at least 95 wt. % and typically higher than 95 wt. %, such as of from 95 wt. % to 99.7 wt. %. The urea melt from the second stage evaporation section is sent to a finishing section (F). Therein a solid urea product (US) is formed, whereby, typically as a result of cooling with an air stream, an ammonia-containing off gas stream (G1) is generated. This stream is subjected to acidic scrubbing in a scrubbing section (AS), thereby removing ammonia in the form of ammonium salts. The scrubbing section produces a scrubbed off-gas (G2), and a utilized scrubbing liquid (SL), which contains the ammonium salts. In accordance with the invention, said utilized scrubbing liquid is sent to a liquid inlet of the second stage evaporation section. In said second stage evaporation section or, as shown, upstream of the inlet thereof, the utilized scrubbing liquid is mixed with the concentrated urea solution obtained from the first stage evaporation section.

Figure 2:
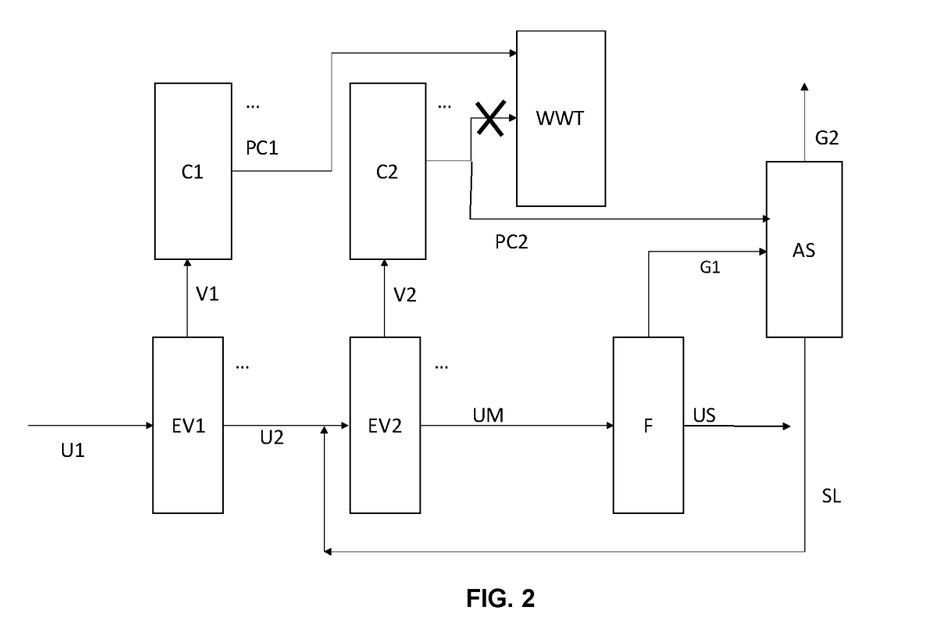
FIG. 2 shows a scheme for the processing as in FIG. 1, in an embodiment involving recycling condensed vapours from evaporation to a urea finishing off-gas treatment section.

FIG. 2 shows a scheme for the processing as in FIG. 1, additionally involving recycling condensed vapours from evaporation to a urea finishing off-gas treatment section. To this end the treatment of the vapours from evaporation is shown. The first stage evaporation section (EV1) has a gas outlet serving to send said vapours (V1) from evaporation to a first stage condensation section (C1), typically a single shell-tube condenser. As conventionally done, the water (condensed vapours or process condensate) (PC1) thereby obtained is sent to a water purification section (also known as a waste water treatment section, WWT).

The second stage evaporation section (EV2) has a gas outlet (V2) to a second stage condensation section (C2), also typically a shell-tube condenser. In accordance with the invention, the water (condensed vapours or process condensate, PC2) obtained from the second stage condensation section are, in deviation from customary practice, not sent to the water purification section (WWT). Rather, these condensed vapours are sent to a liquid inlet of the scrubbing system (AS) in the urea finishing section. It will be understood that therein these condensed vapours (water) are mixed with the scrubbing liquid used in said scrubbing section.

In addition, the following is noted. In a condenser not all of the vapours may become condensed. As a general preference, applicable to this disclosure as a whole, non-condensed vapours are also sent to the scrubbing system. This will generally be from a gas outlet of the condenser to a gas inlet of the scrubbing system.

In sum a method is disclosed for the removal of ammonia from the off-gas of a finishing section of a urea production plant. Also disclosed is a corresponding urea plant, and a method of accordingly modifying a pre-existing urea plant. In a scrubbing section, the off-gas is brought into contact with an acidic scrubbing liquid so as to provide a scrubbed off-gas and a utilized scrubbing liquid comprising ammonium salt. The method specifies an evaporation section, which is part of the urea plant that produces urea melt, that is divided into first and second stages. The first stage is part of the urea melt production plant. The second stage decoupled, as regards recirculation of liquids other than the urea product stream, from the urea melt production plant. This is accomplished by sending utilized scrubbing liquid that contains ammonium salts to the second stage evaporation section, and by sending condensed vapours from said second stage evaporation section to said scrubbing section.

The invention is further explained with reference to Table 1 below. Herein the effect of the embodiment of FIG. 2 is shown, based on model calculations, in various types of urea plants.

TABLE 1

| | Prilling as finishing | Prilling as finishing according to the invention | Granulation as finishing according to the invention |
|---|---|---|---|
| Plant capacity 2000 MTPD About flows and calculated parameters are indicated. | Prilling as finishing [where no dust or acid scrubbing involved for prilling] | [where dust as well as acid scrubbing is considered for prilling] | [Dust as well acidic scrubbing] |
| Total load to water purification section (WWT) | 48 m³/h | 30 m³/h | 32 m³/h |
| NH3 load to water purification section (WWT) | 1700 kg/h | 1300 kg/h | 1340 kg/h |
| H/C for the synthesis (water to carbon ratio) | 0.52 | 0.51 | 0.51 |
| H/U for the synthesis (water to Urea ratio) | 1.90 | 1.88 | 1.88 |

From the Table 1 it is clear that the load of the water purification section (WWT) reduces considerably after implementation of the invention. Clearly less water to be purified is circulating over the absorbers in the urea melt plant.

Although a lower amount of water is circulated over said absorbers, after implementation of the invention the ammonia emissions from the melt plant do not get affected, as this amount of water is advantageously still sufficient for ensuring low NH3 emissions.

A lower amount of water is recycled to synthesis as indicated by synthesis operating parameters at the outlet of the reactor. Both H/C (water to carbon molar ratio based on starting mixture) and H/U (water to urea molar ratio based on actual mixture) reduce after implementing the invention. As a result, the yield of the reactor towards urea slightly increases after implementation of the invention.

The invention claimed is:

1. A method for the removal of ammonia from an off-gas of a finishing section of a urea production plant, wherein the finishing section operates a conversion of a urea melt into solid urea products, thereby generating an ammonia-containing off-gas, the method comprising: obtaining said urea melt by evaporating water from an aqueous urea solution in a first stage evaporation section, so as to form a first water vapour and a concentrated urea solution; further evaporating water from said concentrated urea solution in at least one second stage evaporation section so as to form a second water vapour and the urea melt; subjecting the off-gas to contact with an acidic scrubbing liquid in a scrubbing system so as to provide a scrubbed off-gas and a utilized scrubbing liquid comprising one or more ammonium salts and water; and sending the utilized scrubbing liquid to the second stage evaporation section, thereby subjecting it to evaporation of water together with the concentrated urea solution; and sending said urea melt to the finishing section for conversion of the urea melt into the solid urea products and the ammonia-containing off-gas, wherein all of the urea melt sent to the finishing section comprises the one or more ammonium salts.

2. A method for the production of a solid urea product, comprising producing an aqueous urea solution, evaporating water from said aqueous urea solution in a first stage evaporation section so as to form a first water vapour and a concentrated urea solution, providing all of the concentrated urea solution to a second stage evaporation section and further evaporating water from the concentrated urea solution in the second stage evaporation section to form a second water vapour and a urea melt, and conversion of the urea melt into the solid urea product thereby generating an ammonia-containing off-gas; subjecting said ammonia-containing off-gas to contact with an acidic scrubbing liquid in a scrubbing system so as to provide a scrubbed off-gas and a utilized scrubbing liquid comprising an ammonium salt and water; the method further comprising sending the utilized scrubbing liquid to said second stage evaporation section, thereby subjecting it to evaporation of water together with the concentrated urea solution.

3. The method according to claim 1, further comprising sending the second water vapour to a condensation section so as to form a condensate, and sending the condensate to the scrubbing system.

4. The method according to claim 1, wherein the conversion of the urea melt into the solid urea products, comprises subjecting the melt to prilling or granulation.

5. The method according to claim 2, further comprising sending the second water vapour to a condensation section so as to form a condensate, and sending the condensate to the scrubbing system.

6. The method according to claim 2, wherein the conversion of the urea melt into the solid urea product comprises subjecting the urea melt to prilling or granulation.

7. The method according to claim 4, wherein the conversion of the urea melt into the solid urea products is by fluid-bed or spouted-bed granulation.

8. The method according to claim 4, wherein the conversion of the urea melt into the solid urea products is by prilling.

* * * * *